United States Patent
Flipo et al.

(10) Patent No.: US 7,480,400 B2
(45) Date of Patent: Jan. 20, 2009

(54) DETECTION OF FIBER PATHWAYS

(75) Inventors: Aurelien Flipo, Biot (FR); Mariappan S. Nadar, Plainsboro, NJ (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 199 days.

(21) Appl. No.: 11/657,288

(22) Filed: Jan. 24, 2007

(65) Prior Publication Data
US 2007/0217664 A1 Sep. 20, 2007

Related U.S. Application Data

(60) Provisional application No. 60/783,353, filed on Mar. 16, 2006.

(51) Int. Cl.
*G06K 9/00* (2006.01)
(52) U.S. Cl. ........................ 382/128; 382/225
(58) Field of Classification Search ................ 382/128, 382/131, 173, 225, 286; 345/424; 600/410; 324/307
See application file for complete search history.

(56) References Cited

U.S. PATENT DOCUMENTS

| 6,463,315 | B1 * | 10/2002 | Klingberg et al. | 600/410 |
| 2002/0042569 | A1 * | 4/2002 | Wedeen | 600/411 |
| 2008/0154341 | A1 * | 6/2008 | McIntyre et al. | 607/59 |

OTHER PUBLICATIONS

H.J. Park, et al. "*Clustering Fiber Tracts Using Normalized Cuts. in Seventh International Conference on Medical Image Computing and Computer-Assisted Intervention*" (MICCAI'04), Lecture Notes in Computer Science, pp. 368-375, 2004.

S. Zhang, et al. "*DTI Fiber Clustering in the Whole Brain*" In VIS '04: Proceedings of the conference on Visualization '04, p. 598.28, Washington, DC, USA, 2004. IEEE Computer Society.

J.C. Gore Z. Ding, et al., *Classification and Quantification of Neuronal Fiber Pathways Using Diffusion Tensor MRI*. Magnetic Resonance in medicine, 49:716-721, 2003.

S. Pajevic M. Catani, et al., "*Virtual in Vivo Interactive Dissection of White Matter Fasciculi in the Human Brain*" NeuroImage, 17:77-94, 2002.

A. Vilanova and J. van Wijk B. Moberts. "*Evaluation of Fiber Clustering Methods for Diffusion Tensor Imaging*" In VIS '05: Proceedings of the conference on Visualization '05. IEEE Computer Society, 2005.

* cited by examiner

*Primary Examiner*—Phuoc Tran
(74) *Attorney, Agent, or Firm*—Donald B. Paschburg; F. Chau & Associates, LLC

(57) ABSTRACT

A computer-implemented method for detection of fiber pathways includes determining initial data as a subset of voxels that have been selected from a diffusion tensor image by applying a threshold to fractional anisotropy values, determining a cluster of points with highly collinear diffusion directions, and performing region growth to find suitable seed points in a plane that is normal to the cluster's mean direction, starting from the center of the cluster. The method further includes tracing pathways from the seed points, eliminating voxels of the subset from the initial data that are close to any of the pathways using a distance threshold, displaying a visualization of a selection of voxels used as seed points and of the pathways traced from the seed points.

10 Claims, 3 Drawing Sheets

DETECTION OF FIBER PATHWAYS

CROSS-REFERENCE TO RELATED APPLICATIONS

This application claims the benefit of Provisional Application No. 60/783,353 filed on Mar. 16, 2006 in the United States Patent and Trademark Office, the content of which is herein incorporated by reference in its entirety.

BACKGROUND OF THE INVENTION

1. Technical Field

The present disclosure relates to fiber tracking, and more particularly to fiber tracking in a diffusion tensor image dataset.

2. Description of Related Art

Diffusion tensor image scans comprise at least six gradient directions, sufficient to determine a diffusion tensor in, for example, a brain scan. From the diffusion tensor, diffusion anisotropy measures such as the Fractional Anisotropy (FA) can be determined. Moreover, the principal direction of the diffusion tensor can be used to infer white-matter connectivity of the brain and model it as a tract.

Fiber tracking is the process of detecting fiber pathways in a DTI dataset by following directional information contained in the diffusion tensors. Various methods can be applied to determine a set of tracks to represent white-matter connectivity of the brain; typically they rely on the placement of starting points or seed points, and tracking fiber pathways from these starting positions according to direction and anisotropy data determined from the diffusion tensors.

Seed points can be placed manually by the user by selecting a region of interest, or automatically by selecting a subset of voxels that match a specific criterion (e.g. FA threshold). In both cases, the resulting set of fiber pathways can be highly redundant, wherein many fibers can have similar trajectories, and some relevant pathways can be ignored if the proper seed points were not selected. Furthermore, these methods can yield very large sets of seed points, making the fiber tracking process and any further data analysis computationally expensive.

Therefore, a need exists for a system and method for automatic detection of fiber pathways in a DTI dataset.

SUMMARY OF THE INVENTION

According to an embodiment of the present disclosure, a computer-implemented method for the detection of fiber pathways includes determining initial data as a subset of voxels that have been selected from a diffusion tensor image by applying a threshold to fractional anisotropy values, determining a cluster of points with highly collinear diffusion directions, and performing region growth to find suitable seed points in a plane that is normal to the cluster's mean direction, starting from the center of the cluster. The method further includes tracing pathways from the seed points, eliminating voxels of the subset from the initial data that are close to any of the pathways using a distance threshold, and displaying a visualization of a pruned subset of voxels of the diffusion tensor and a visualization of the pathways traced from the seed points.

According to an embodiment of the present disclosure, a computer readable medium is provided embodying instructions executable by a processor to perform a method for fiber tracking. The method includes determining a subset of voxels selected from an input diffusion tensor image by applying a threshold to fractional anisotropy values of the voxels, determining a cluster of points with collinear diffusion directions, performing region growth to find seed points in a plane that is normal to the cluster's mean direction, starting from a center of the cluster, tracing pathways from the seed points, eliminating voxels of the subset that are close to the pathways using a distance threshold, displaying a visualization of a selection of voxels used as seed points, and displaying a visualization of the pathways traced from the seed points.

BRIEF DESCRIPTION OF THE DRAWINGS

Preferred embodiments of the present invention will be described below in more detail, with reference to the accompanying drawings.

DETAILED DESCRIPTION OF PREFERRED EMBODIMENTS

Fiber tracking is the process of detecting fiber pathways in a DTI dataset by following directional information contained in the diffusion tensors. Various techniques can be applied to perform this operation, but they all rely on the same principle. The method uses the information contained in the tensor situated at this position to start building a chain of points that represent the fiber.

In most cases, the seed points are placed manually in a region of interest. Sometimes, seed points can also be placed in the whole volume: in that case, a subset of voxels is usually selected by applying a threshold (e.g., using FA values). However, this method is not entirely satisfactory: on a typical brain dataset, even after applying a high FA threshold (e.g., 0.80 or more), the number of seed points can be too big and result in high computation times for the fiber tracking step. It should be noted that seed points detected with this method are highly redundant: a fiber pathway tracked from a particular seed point is likely to go through many other seed points, making them useless. This redundancy can be a problem for further analysis of the pathways: for example, statistical methods can be biased if many pathways share similar trajectories.

According to an embodiment of the present disclosure, to solve this problem, a method for fiber tracking allows the automatic detection of fiber pathways with a minimal number of seed points. The aim of this method is to obtain enough pathways to have a good representation of the connectivity between regions of the dataset, while keeping a reasonably low number of fibers by avoiding any redundancy.

Figure 1:
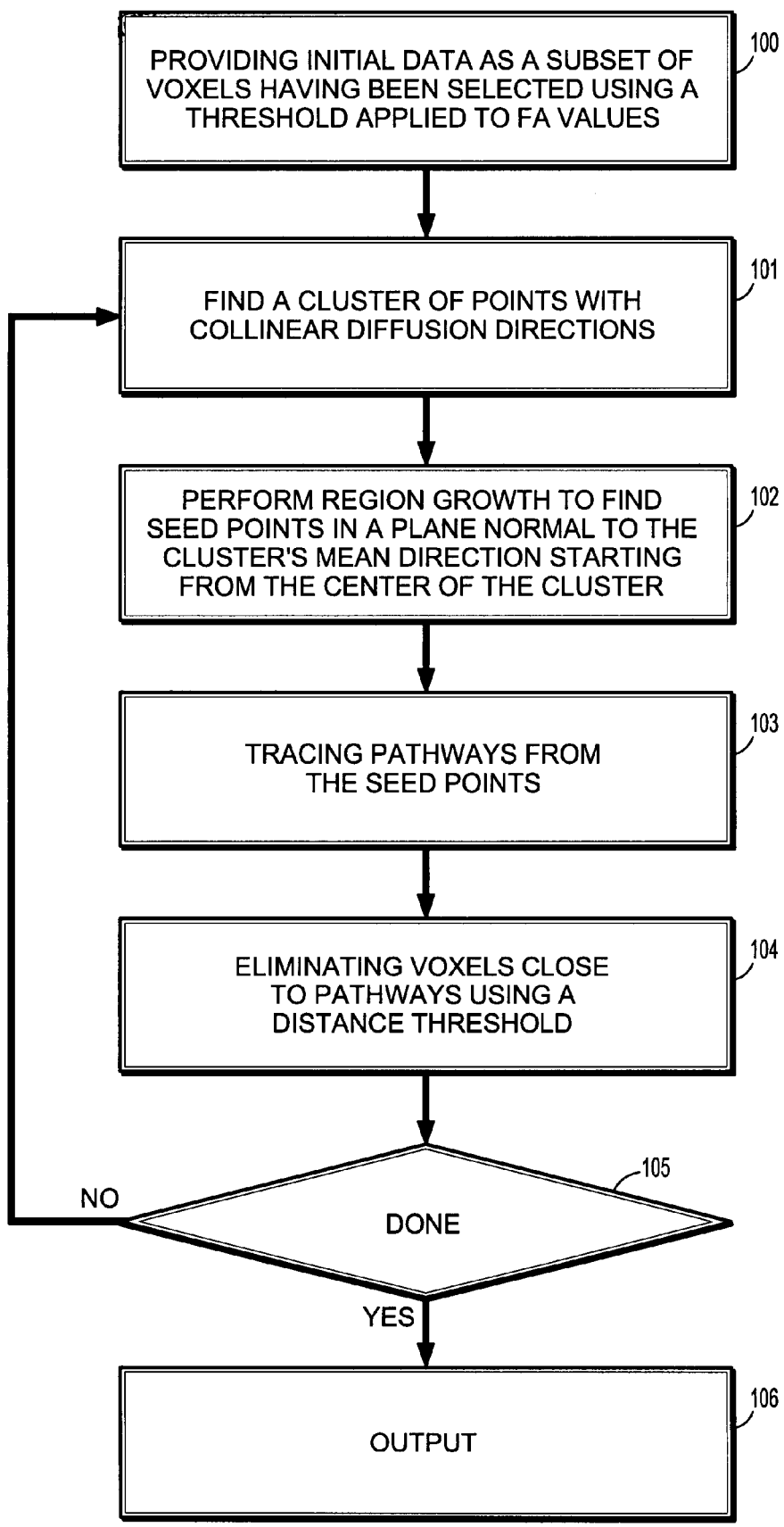
FIG. 1 is a flow chart of a method for the detection of fiber pathways according to an embodiment of the present disclosure.

Referring to FIG. 1, a method for fiber tracking is iterative. The method repeats until the desired result is reached. The initial data is the subset of voxels that have been selected by applying a threshold to the FA values 100. Using a classification algorithm, the method finds a cluster of points with highly collinear diffusion directions 101. The method includes performing region growth to find suitable seed points in a plane that is normal to the cluster's mean direction, starting from the center of the cluster 102. The pathways are traced from the seed points 103. In the initial subset of voxels, those voxels that are close enough to any of the pathways are eliminated using a distance threshold 104. The method repeats a fixed number of iterations or until not enough voxels are left to define a cluster 105 at block 101. Results, the selection of voxels used as seed points may be stored to a computer readable media or displayed in a diffusion tensor visualization 106. These voxels constitute a minimal set of seed points yielding fiber pathways that can be used to visualize white-matter connectivity on the whole brain.

Voxel classification 101 aims to find a region in which there is a high concentration of voxels with similar principal directions. If a cluster of voxels with these properties can be formed, it is likely that a bundle of fibers is going through that region. Such a cluster can be isolated by using two classification steps on the current set of voxels.

The voxels are clustered according to their principal directions (using the k-means algorithm and a directional metric known as Watson's model). This leads to a certain number of directional clusters, e.g., subsets of voxels with similar directions. The biggest of these clusters is then isolated, and another classification step is performed on this subset, this time with a Euclidian metric. The biggest resulting cluster has the desirable properties of containing only voxels with similar principal directions, and located in the same region of the data space. The center of this cluster can be used as a starting point for seeding using region growth.

Region growth 102 includes defining a set of seed points by performing region growth on a plane, starting from an initial seed point. Here, the points located in the initial point's neighborhood are examined to determine if they can be used as seed points. The neighborhood is defined as the plane that contains the initial point and is normal to the principal direction of the tensor at this point. In this plane, a propagation method selects a number of seed points by checking neighbors around the initial point. A neighboring point will be selected for seeding if the tensor at this point has a similar direction (e.g., difference<angle threshold), and if its FA is high enough (FA>threshold).

Fiber tracking 103 may be implemented using known methods applied to the defined set of seed points to determine pathways that run through these points. Exemplary methods for fiber tracking include, but are not limited to, flow-based fiber tracking, curve propagation using a principle eigenvector field, multi-tensor modeling, diffusion spectrum imaging, etc.

Voxel elimination 104 is used to avoid redundancy: if a voxel belongs to one of the previously determined pathways, then it is not suitable as a seed point for the next clustering. Before moving on to the next clustering, voxels that are too close to one of the new pathways (e.g., distance<threshold) will be removed from the clustering set.

A method according to an embodiment of the present disclosure has been found to yield good graphical representations of the dataset, with a much lower number of fibers than what could be observed by finding seed points only by thresholding. For a typical dataset (128×128×60 brain dataset), a thresholding with $FA_{min}=0.80$ yields 2124 seed points (and the same number of fibers). From this initial set of voxels, the method retains only 483 seed points after 100 iterations, while keeping a similar visual aspect for the complete set of pathways.

Figure 2C:
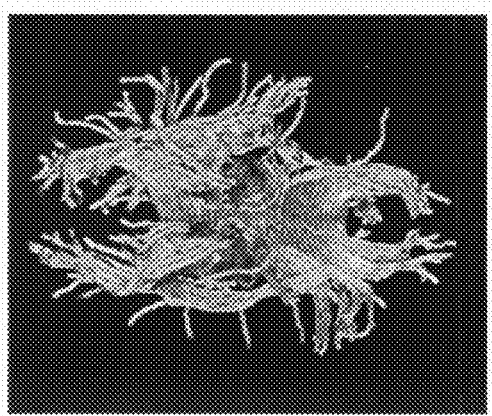
FIGS. 2A-E is a series of results at 5, 10, 20, 50 and 100 iterations according to an embodiment of the present disclosure.
Figure 2F:
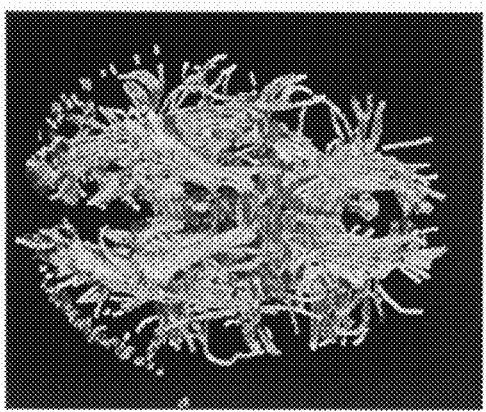
FIG. 2F depicts the results of fiber tracking when all of the voxels in the initial dataset are used as seed points.
Figure 2B:
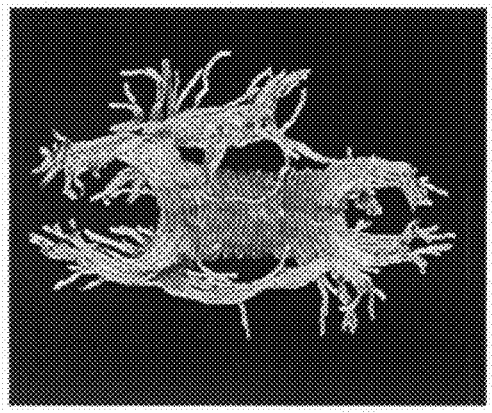
Figure 2E:
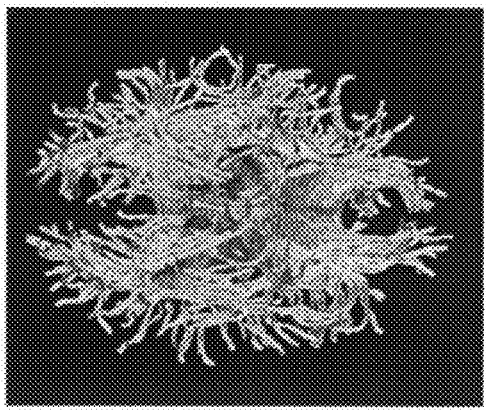
Figure 2A:
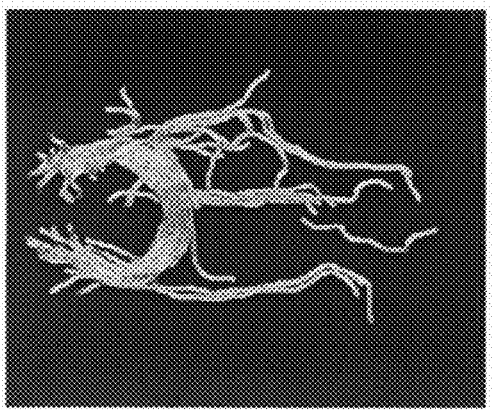
Figure 2D:
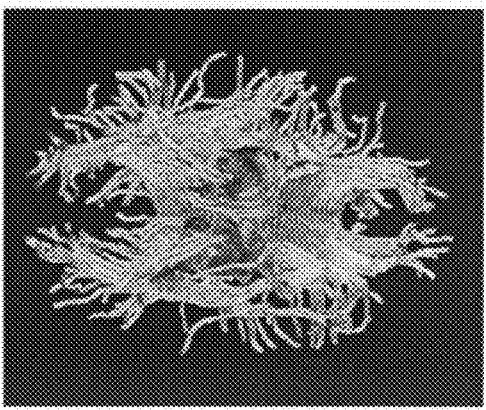

FIGS. 2A-E show results of the method after 5, 10, 20, 50 and 100 iterations, respectively. The lower-right shows all voxels in the initial set are used as seeding points. FIG. 2F shows the results of fiber tracking when all of the voxels in the initial dataset are used as seed points.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

Figure 3:
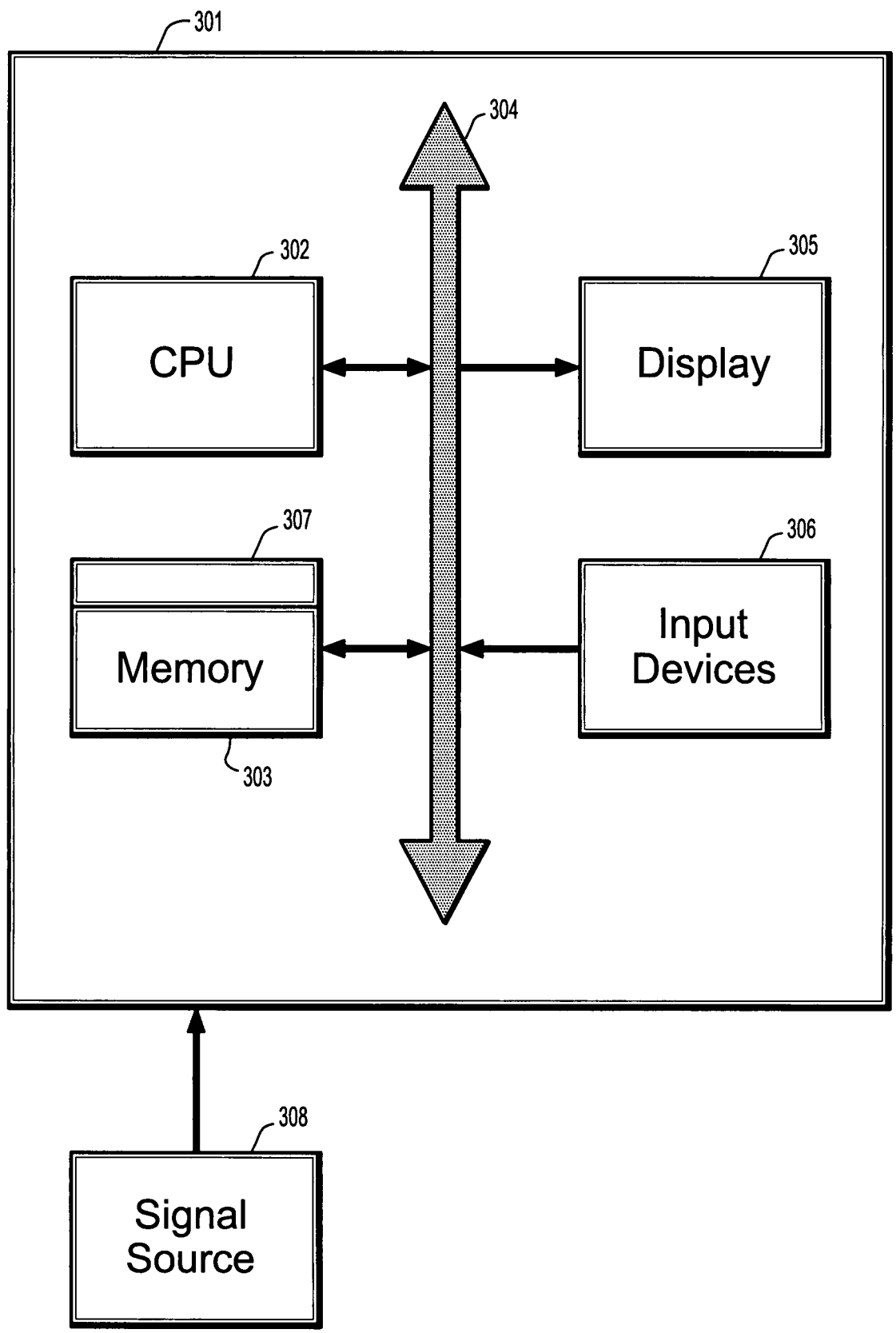
FIG. 3 is a diagram of a system according to an embodiment of the present disclosure.

Referring to FIG. 3, according to an embodiment of the present disclosure, a computer system 301 for the detection of fiber pathways can comprise, inter alia, a central processing unit (CPU) 302, a memory 303 and an input/output (I/O) interface 304. The computer system 301 is generally coupled through the I/O interface 304 to a display 305 and various input devices 306 such as a mouse and keyboard. The support circuits can include circuits such as cache, power supplies, clock circuits, and a communications bus. The memory 303 can include random access memory (RAM), read only memory (ROM), disk drive, tape drive, etc., or a combination thereof. The present invention can be implemented as a routine 307 that is stored in memory 303 and executed by the CPU 302 to process the signal from the signal source 308. As such, the computer system 301 is a general-purpose computer system that becomes a specific purpose computer system when executing the routine 307 of the present disclosure.

The computer platform 301 also includes an operating system and microinstruction code. The various processes and functions described herein may either be part of the microinstruction code or part of the application program (or a combination thereof), which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Having described embodiments for a system and method for the detection of fiber pathways, it is noted that modifications and variations can be made by persons skilled in the art in light of the above teachings. It is therefore to be understood that changes may be made in embodiments of the present disclosure that are within the scope and spirit thereof.

What is claimed is:

1. A computer-implemented method for detection of fiber pathways comprising:
   determining a subset of voxels selected from an input diffusion tensor image by applying a threshold to fractional anisotropy values of the voxels;
   determining a cluster of points with collinear diffusion directions;
   performing region growth to find seed points in a plane that is normal to the cluster's mean direction, starting from a center of the cluster;
   tracing pathways from the seed points;
   eliminating voxels of the subset that are close to the pathways using a distance threshold;
   displaying a visualization of a selection of voxels used as seed points; and
   displaying a visualization of the pathways traced from the seed points.

2. The computer-implemented method of claim 1, further comprising using the pruned subset as a basis for a next iteration comprising:
- determining a next cluster of points with collinear diffusion directions;
- performing region growth to find seed points in a plane that is normal to the next cluster's mean direction, starting from a center of the next cluster;
- tracing pathways from the seed points;
- eliminating voxels of the subset that are close to the pathways using the distance threshold; and
- displaying a next visualization of a next selection of voxels used as seed points.

3. The computer-implemented method of claim 1, wherein the method iterates for a fixed number of iterations.

4. The computer-implemented method of claim 1, wherein the method iterates until not enough voxels are left to determine a cluster.

5. The computer-implemented method of claim 1, wherein eliminating voxels further comprises:
- determining if a voxel belongs to a previously determined pathway; and
- eliminating the voxel as a potential seed point for a next clustering iteration upon determining that the voxel belongs to the previously determined pathway.

6. A computer readable medium embodying instructions executable by a processor to perform a method for fiber tracking, the method comprising:
- determining a subset of voxels selected from an input diffusion tensor image by applying a threshold to fractional anisotropy values of the voxels;
- determining a cluster of points with collinear diffusion directions;
- performing region growth to find seed points in a plane that is normal to the cluster's mean direction, starting from a center of the cluster;
- tracing pathways from the seed points;
- eliminating voxels of the subset that are close to the pathways using a distance threshold;
- displaying a visualization of a selection of voxels used as seed points; and
- displaying a visualization of the pathways traced from the seed points.

7. The method of claim 6, further comprising using the pruned subset as a basis for a next iteration comprising:
- determining a next cluster of points with collinear diffusion directions;
- performing region growth to find seed points in a plane that is normal to the next cluster's mean direction, starting from a center of the next cluster;
- tracing pathways from the seed points;
- eliminating voxels of the subset that are close to the pathways using the distance threshold; and
- displaying a next visualization of a next selection of voxels used as seed points.

8. The method of claim 6, wherein the method iterates for a fixed number of iterations.

9. The method of claim 6, wherein the method iterates until not enough voxels are left to determine a cluster.

10. The method of claim 6, wherein eliminating voxels further comprises:
- determining if a voxel belongs to a previously determined pathway; and
- eliminating the voxel as a potential seed point for a next clustering iteration upon determining that the voxel belongs to the previously determined pathway.

* * * * *